(12) United States Patent
Siemers

(10) Patent No.: US 8,802,030 B2
(45) Date of Patent: Aug. 12, 2014

(54) CAPILLARY DISPENSER

(75) Inventor: Adrian Siemers, Jena (DE)

(73) Assignee: Cybio AG, Jena (DE)

( * ) Notice: Subject to any disclaimer, the term of this patent is extended or adjusted under 35 U.S.C. 154(b) by 212 days.

(21) Appl. No.: 13/363,426

(22) Filed: Feb. 1, 2012

(65) Prior Publication Data

US 2013/0195733 A1     Aug. 1, 2013

(51) Int. Cl.
     *B01L 3/02*          (2006.01)

(52) U.S. Cl.
USPC ........ 422/520; 422/501; 422/522; 73/864.02; 73/864.13; 73/864.16; 73/864.17

(58) Field of Classification Search
USPC .......... 422/501, 520, 522; 73/864.02, 864.13, 73/864.16–864.18
See application file for complete search history.

(56) References Cited

U.S. PATENT DOCUMENTS

| | | | |
|---|---|---|---|
| 4,140,488 A | 2/1979 | Mack et al. | |
| 4,900,515 A * | 2/1990 | Xalabarder Miramanda | 422/516 |
| 5,059,398 A | 10/1991 | Kenney | |
| 5,508,200 A | 4/1996 | Tiffany et al. | |
| 5,736,105 A * | 4/1998 | Astle | 422/509 |
| 6,713,021 B1 * | 3/2004 | Shvets et al. | 422/502 |
| 7,438,857 B2 * | 10/2008 | Massaro | 422/509 |
| 2003/0228241 A1 | 12/2003 | Legge | |
| 2004/0141885 A1 * | 7/2004 | Godin et al. | 422/100 |
| 2005/0112776 A1 | 5/2005 | Clark et al. | |
| 2005/0244303 A1 | 11/2005 | Ingenhoven et al. | |

FOREIGN PATENT DOCUMENTS

| | | |
|---|---|---|
| DE | 19742005 A1 | 4/1999 |
| EP | 1506814 A1 | 2/2005 |
| GB | 2368640 A | 5/2002 |
| WO | WO 2003/039751 A1 | 5/2003 |

* cited by examiner

*Primary Examiner* — Jan Ludlow

(74) *Attorney, Agent, or Firm* — Leydig, Voit & Mayer, Ltd.

(57) ABSTRACT

A capillary dispenser includes at least one plunger-cylinder unit having a cylinder module and a plunger module disposed together on an axis. The cylinder module has an inner cylinder that is pneumatically connected to at least one capillary. The plunger module includes a hollow plunger that is closable on one side and is movable in the inner cylinder along the axis between an upper end position and a lower end position of the plunger module.

10 Claims, 6 Drawing Sheets

Section B-B

CAPILLARY DISPENSER

BACKGROUND

British patent specification GB 23 686 40 B describes an approach in which a dispenser for dispensing minute volumes is provided with capillaries with which a liquid that is to be dispensed is picked up by means of the capillary effect. In order to dispense the liquid held in the capillaries, an excess pressure is generated at one end of the capillaries. This can be done either individually or preferably for all of the capillaries together by connecting them to a shared pressure chamber.

A dispenser described here consists of a plurality of capillaries that are open on both sides, a source of compressed air, a valve for switching the compressed air on and off, a pressure chamber consisting of an upper part with a compressed-air inlet and a lower part in which the capillaries are held. The upper part and the lower part of the pressure chamber are sealed off with respect to each other, so that when the pressure chamber is charged with compressed air, the compressed air is distributed uniformly over the capillaries and the liquid contained in the capillaries is expelled.

A considerable disadvantage of such a capillary dispenser is that the capillaries are emptied in parallel by means of a shared source of pressure. In order to reliably empty all of the capillaries completely, it is necessary to work at a high pressure since capillaries that have already been emptied function as a "short-circuit" and the compressed air can escape from these capillaries with relatively little resistance. Typical operating pressures here are 15 to 25 psi or 1.0 to 1.7 bar.

The subsequently incoming air exits the capillaries at a speed of several meters per second and the expelled volume of air can amount to a few milliliters, depending on the size of the pressure chamber, on the pressure applied and on the number of capillaries. This fact considerably diminishes the usefulness of this technology.

Dispensing discrete drops onto a "smooth" surface such as, for example, a specimen slide, is very difficult or even impossible since the subsequently incoming air disperses the drops and distributes them over the surface. For this reason, the only option is to dispense the liquid into wells of so-called microtiter plates. However, there are limitations here as well; for instance, liquid can only be dispensed into empty wells since the subsequently incoming air can cause splashing in the wells that are already filled with liquid, thus leading to cross-contamination between the individual wells.

For this reason, such capillary dispensers are designed purely for dispersing liquid into empty wells. This, however, does not completely eliminate the problem of cross-contamination. The capillaries are never completely emptied right away. When the liquid is expelled, a liquid film remains on the inside of the capillary and it only moves slowly towards the end of the capillary as a result of the force of gravity and the subsequently incoming air. Here, due to the high flow rate of the air, the film is atomized into an aerosol. When sufficiently sensitive measuring equipment is employed, this aerosol can also be detected as cross-contamination due to the high concentration of active ingredient that is present there.

In the search for a solution to the above-mentioned problems, the person skilled in the art will also turn to the state of the art of the type known from liquid-handling systems equipped with pipettes.

The person skilled in the art of liquid-handling systems is familiar with so-called air-displacement pipettes that make use of a plunger-cylinder unit with which liquid can be picked up and dispensed by means of a pipette tip connected to said unit.

The pipette tip here is fastened to an opening in the face of the inner cylinder. The plunger is arranged inside the inner cylinder so that it can move on a shared axis and so as to be sealed off with respect to the inner cylinder. Raising or lowering the plunger inside the inner cylinder increases or decreases the free volume of the inner cylinder associated with the pipette tip, as a result of which a liquid can be picked up or dispensed via the pipette tip, corresponding to the change in volume.

If a capillary were to be installed instead of a pipette tip, the capillary effect would cause the capillary to already automatically fill up when it is dipped into the liquid since the free volume of the inner cylinder is quite large relative to the volume of the capillary. Therefore, it would not be necessary to lift the plunger in the inner cylinder in order to pick up liquid through the capillary.

The capillary, however, could be emptied according to the principle of air displacement in that the free cylinder volume is reduced by lowering the plunger in the inner cylinder, so that the air contained therein is expelled via the capillary.

If a plunger is provided for each individual capillary, the air displacement could be dosed in very fine increments. This allows the formation of a drop on the free end of the capillary that can be deposited systematically by making contact with, for instance, a specimen slide.

If the acceleration and the achievable speed of the plunger are high enough, a free-falling drop or liquid jet can also be dispensed contact-free. The pressure needed in this case for an individual capillary is smaller than when all of the capillaries are blown free together since the pressure does not have to be over-dimensioned as is necessary in view of the possibility of "short-circuits" of the type described in the state of the art.

Experiments have shown that the free volume of the inner cylinder displaced by the plunger and thus the amount of air subsequently flowing out of the capillaries was less than 50 µl and thus smaller by a factor of 20 to 200 than with a capillary dispenser in which all of the capillaries are connected to a pressure chamber.

This smaller volume of expelled air, with the concurrent lower pressure and thus lower dispensing speed, make it possible to dispense onto smooth surfaces as well as into vessels that already contain a liquid such as the wells of a microtiter plate. This also largely prevents the formation of aerosols.

When it comes to the above-mentioned advantages, as far as the form is concerned, the use of plunger-cylinder units that are each connected to a capillary seems to be evident to the person skilled in the art. The disadvantages associated with a capillary instead of a pipette, however, will preclude the person skilled in the art from pursuing such an idea.

After each dispensing procedure, the plunger must be returned to the initial position without inadvertently picking up any liquid in this process before it is ready to be used again for dispensing. This entails the risk that, if there is any residual liquid present in the capillaries or if the equipment is operated incorrectly (.e.g. the capillaries are still immersed in the liquid), liquid will be drawn up into the inner cylinder, and the function of the dispenser is no longer ensured.

SUMMARY OF THE INVENTION

In an embodiment, the present invention provides a capillary dispenser including at least one plunger-cylinder unit having a cylinder module defining an axis and a plunger module disposed on the axis. The cylinder module has an inner cylinder that is pneumatically connected to at least one capillary. The plunger module includes a hollow plunger that is closable on one side and is movable in the inner cylinder along the axis between an upper end position and a lower end position of the plunger module.

BRIEF DESCRIPTION OF THE DRAWINGS

Exemplary embodiments of the present invention are explained in greater detail below with reference to the drawings, in which:

FIG. 1b shows a detailed view of the module according to FIG. 1a;

FIG. 2 shows a sectional view of the module according to FIG. 1a;

DETAILED DESCRIPTION

Figure 1A:
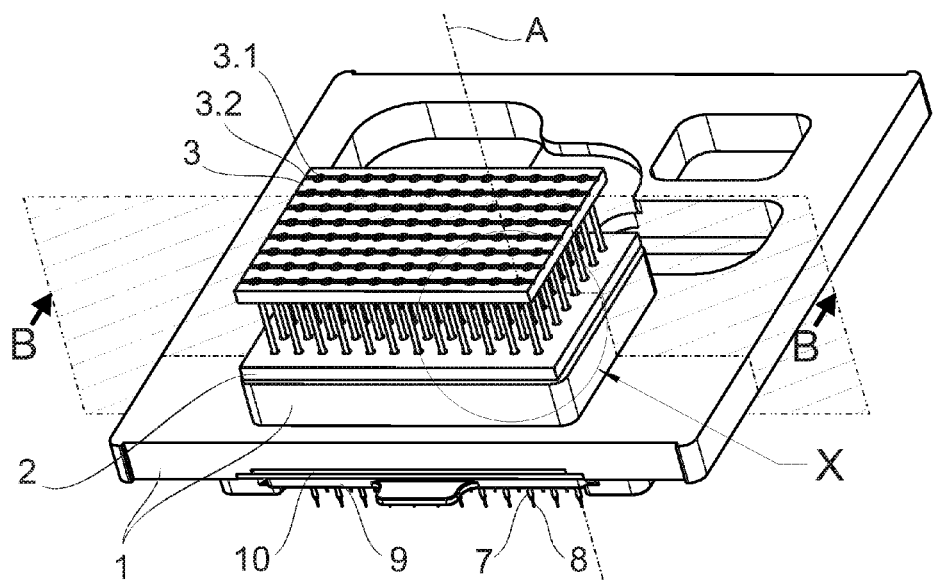
FIG. 1a shows a perspective view of a module of a capillary dispenser.

In an embodiment, the present invention provides a capillary dispenser that has at least one plunger-cylinder unit and that employs structural measures to reliably prevent liquid from being accidentally picked up.

Advantageously, it should be possible to modify the capillary dispenser with just a few structural changes in order to optimize it either for contactless dispensing into liquids or for dispensing while the capillaries make contact.

Advantageously, it should be possible to quickly replace the capillaries at a high repeat rate.

Fundamentally, a capillary dispenser according to an embodiment of the invention can be fitted with just one capillary, with several capillaries in a row or with several capillaries in a matrix. The capillaries can each be associated with a plunger-cylinder unit, or else several capillaries are connected to a shared cylinder and are thus associated with a shared plunger-cylinder unit 17.

Since a capillary dispenser is fundamentally set up in such a way that it dispenses in the direction of the gravitational force, the terms "up" and "down" used in the elaborations below are unambiguous. They are also to be construed in this manner when a capillary dispenser is operated so that it acts in a direction that is not vertical, for which there are applications, especially for capillary dispensers with only one capillary.

When the structure and the mode of operation of a capillary dispenser are described below on the basis of a plunger-cylinder unit 17, the statements made pertaining thereto also apply to all of the plunger-cylinder units of the capillary dispenser.

As a matter of principle, the capillary dispenser according to an embodiment of the invention has at least one plunger-cylinder unit 17 consisting of a cylinder module 16 with an inner cylinder 1.1 and a plunger module 15 having a plunger 5. The inner cylinder 1.1 and the plunger 5 are arranged coaxially to each other on an axis A, whereby the plunger 5 is sealed off with respect to the inner cylinder 1.1, inside of which it can be moved along the axis A by a path of travel. Even though it is fundamentally possible to initiate the movement manually, it is the case that, especially when the capillary dispenser has a large number of capillaries 8, it is controlled by means of motor, for which purpose the capillary dispenser has a drive and a control unit.

The plunger 5 is a hollow plunger that is opened at the beginning of its movement towards the upper end position of the plunger module 15, and it remains open on both sides over the length of the path of travel.

During the movement towards a lower end position of the plunger module 15, at the beginning, the plunger 5 is closed on one side and it remains closed on one side over the entire length of the path of travel. The upper and lower end positions of the plunger module 15 limit the path of travel. The inner cylinder 1.1 is pneumatically connected to at least one capillary 8.

Since the plunger 5 is open during its movement towards the upper end position of the plunger module 15 and since the plunger-cylinder unit 17 thus constitutes an open system, the pressure conditions do not change at the end of the at least one capillary 8 that is in communication with the inner cylinder 1.1 while the plunger 5 is being moved towards the upper end position of the plunger module 15. Therefore, this movement does not have any influence on the pressure conditions present in the capillary 8. In other words, the capillary 8 could already be filled or it could be simultaneously filled exclusively through the capillary effect if its other end (hereinafter referred to as the free end) is in contact with a liquid.

When the plunger 5 is moved towards the lower end position of the plunger module 15, it is closed, and the plunger-cylinder unit 17 thus constitutes a closed system. The air present in the plunger-cylinder unit 17 is compressed, as a result of which the pressure at the end of the at least one capillary 8 that is in contact with the inner cylinder 1.1 increases steadily while the plunger 5 is moved towards the lower end position of the plunger module 15. The air escapes via the at least one capillary 8, as a result of which liquid present there is blown out.

Since the plunger 5 is opened (vented) every time the capillary 8 has been emptied, that is to say, the plunger module 15 is moved at least a small portion of the path of travel in the direction of the upper end position of the plunger module 15, it is advantageous for the length and the cross section of the plunger 5 and of the inner cylinder 1.1 to be dimensioned in such a way that the path of travel is just sufficient to empty the capillary 8. Thus, the entire path of travel is fully utilized with each emptying and venting procedure, and the inner cylinder 1.1 and the plunger 5 can be dimensioned as small as possible.

The dimensions can also be selected such that one path of travel is sufficient to empty the capillary 8 multiple times. In order to empty and re-fill the capillary 8, the plunger module 15 is then raised just slightly in the direction of the upper end position so that the capillary 8 opens.

Since the pressure in the inner cylinder 1.1 does not rise abruptly and it is only relatively low, the liquid can also be dispensed into a vessel that already contains a liquid without this causing cross-contamination of the type cited in the description of the state of the art. Pulsed dispensing is also possible if a valve 14 is provided in the connection between the inner cylinder 1.1 and the capillary 8.

Fundamentally, it is immaterial for the functioning of the plunger-cylinder unit 17 where the plunger 5 is closed. Theoretically, this can be at the lower end, which is inside the inner cylinder 1.1, elsewhere inside or preferably at the upper end of the plunger 5.

Preferably, the plunger 5 is closed by means of a plunger seal. Either the face of the plunger 5, which is advantageously configured so as to be rounded off and situated at the upper end, is placed directly against the plunger seal, or else it is sealed indirectly in that a plunger head 5.1 that is provided around the end of the plunger 5 and that seals off its circumference is placed against the plunger seal. The latter arrangement has the advantage that the dimensioning of the plunger head 5.1 serves to create a wider contact surface area. The plunger seal can preferably be configured in the form of a plunger sealing plate 6 made of an elastic material, for example, an elastomer. All of the plungers 5 are then advantageously sealed by the same plunger sealing plate 6. Instead of this, individual cones or balls 12 can also be employed as the plunger seal. These cones or balls 12 can be made, for example, of glass, ceramic or, likewise preferred, of an elastic material. The plunger 5 is suspended in the plunger module 15 by means of the plunger head 5.1.

A few embodiments will be described below which differ from each other in that they have different structural configurations of various components such as the head seal, the plunger head 5.1, the valve 14 and the capillary holder 7. The various configurations for the various components can be combined among each other, even if not every conceivable combination is expressly mentioned here.

An advantageous embodiment that best meets requirements made in terms of the precision and speed for dispensing minute volumes is a capillary dispenser having a plurality of capillaries 8 that are arranged with respect to each other in a matrix that matches the wells of commercially available microtiter plates, and a plunger-cylinder unit 17 is present for each capillary 8.

Figure 1B:
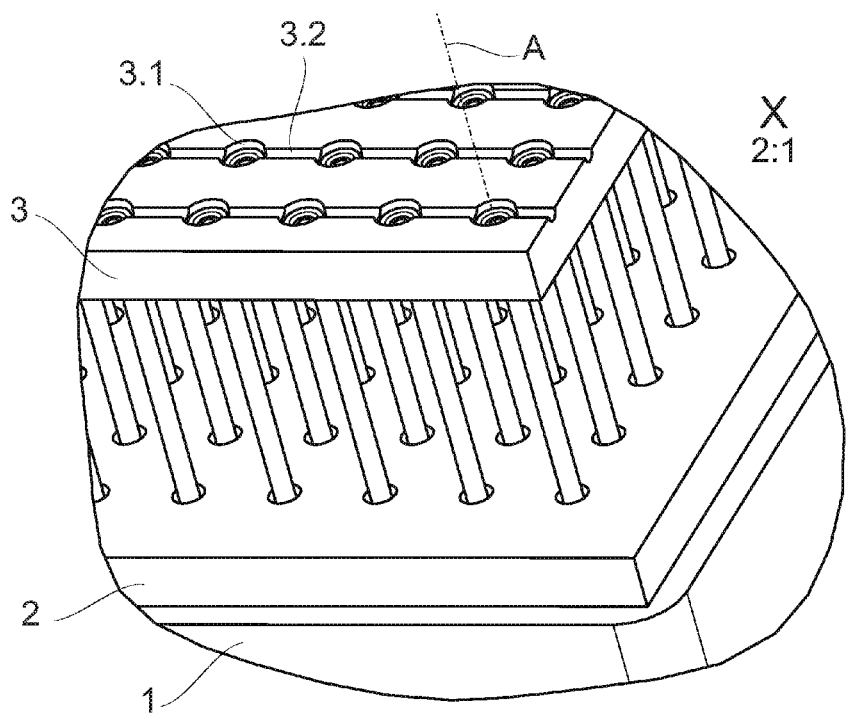
Figure 2:
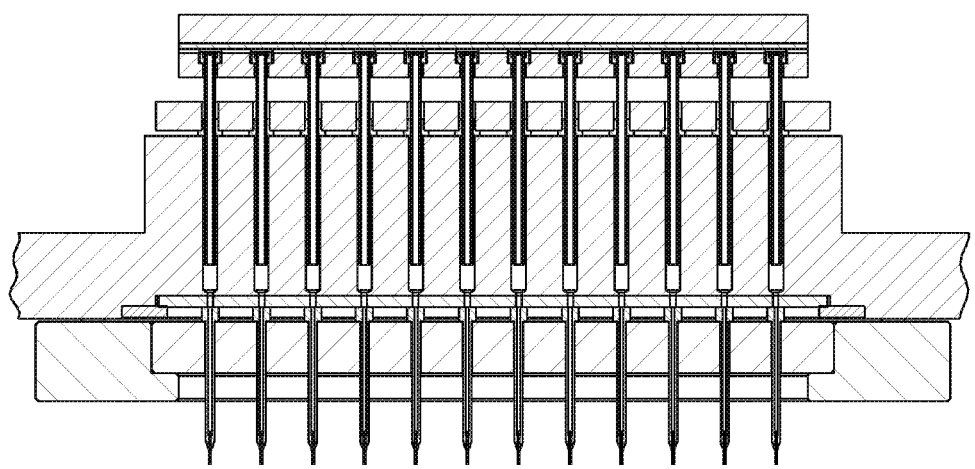

Such a capillary dispenser will be elaborated upon in an embodiment on the basis of FIGS. 1 to 3.

The capillary dispenser shown in FIG. 1a with a matrix-like arrangement of capillaries 8 has a carrier plate 1, a pressure plate 2 and a plunger holding plate 3 as well as a cartridge 9 which rests directly on the carrier plate 1 via a sealing mat 10 and in which the capillary holders 7, along the capillaries 8, are suspended, thus creating a positive fit with the sealing mat 10.

For each capillary 8, there is one plunger-cylinder unit 17, in each case arranged on an axis A. One of the axes A has been drawn in FIG. 1 by way of an example. In order to allow a view of the plunger holding plate 3, a plunger sealing plate 6 that covers the plunger holding plate 3 as well as a stop plate 4 arranged over it—both of which are likewise associated with the plunger-cylinder units 17—are not shown in FIG. 1a.

The recesses depicted in the carrier plate 1 are provided for the modules needed for automatic operation such as, for instance, the control module, the motor and the gears. The carrier plate 1 at the same time forms the bottom of a housing.

Various embodiments of the plunger-cylinder unit 17 are shown as sectional views in FIGS. 2 to 5.

Figure 3A:
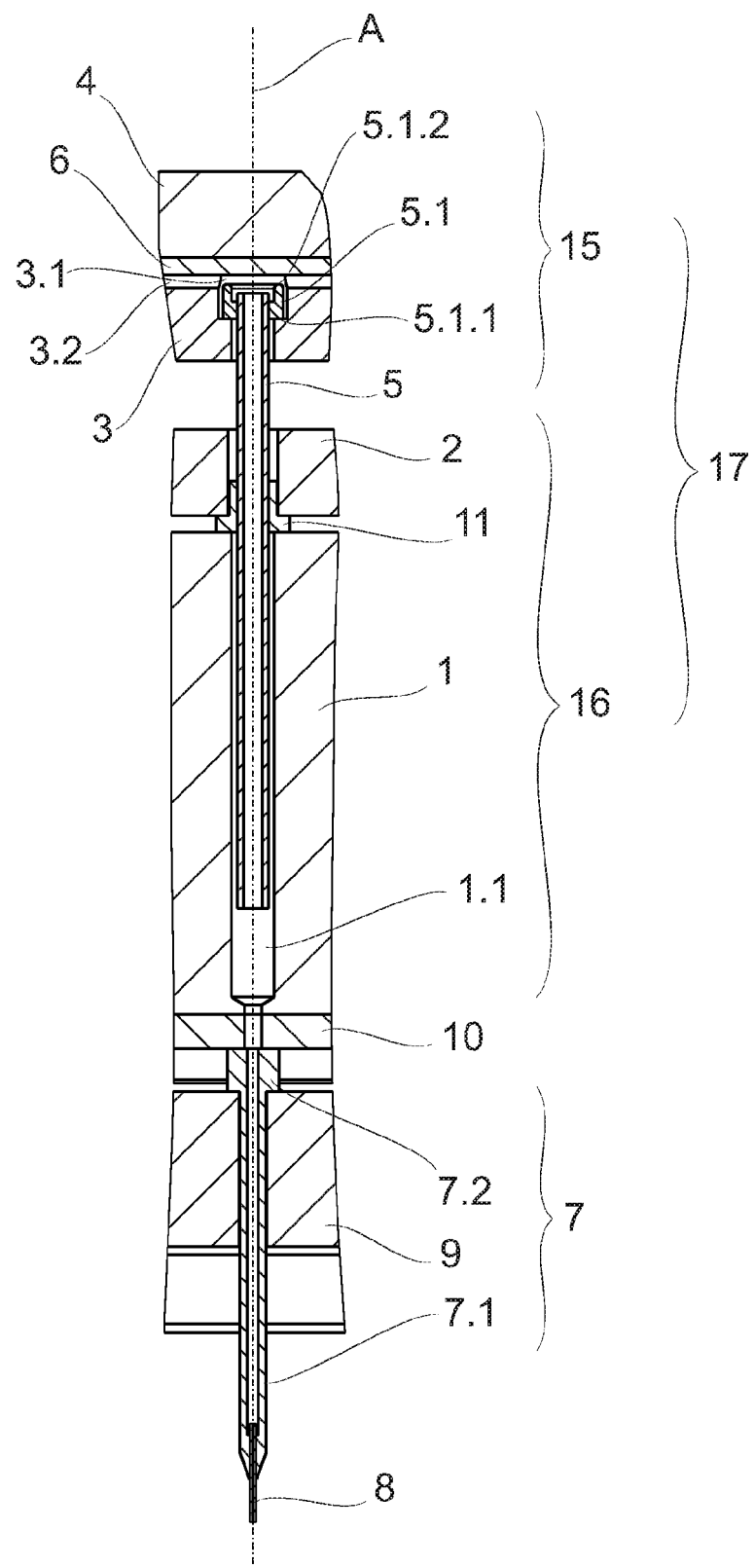
FIG. 3a shows a plunger-cylinder unit with an embodiment of a plunger sealed by a plunger sealing plate, with the plunger module in an upper end position.
Figure 3B:
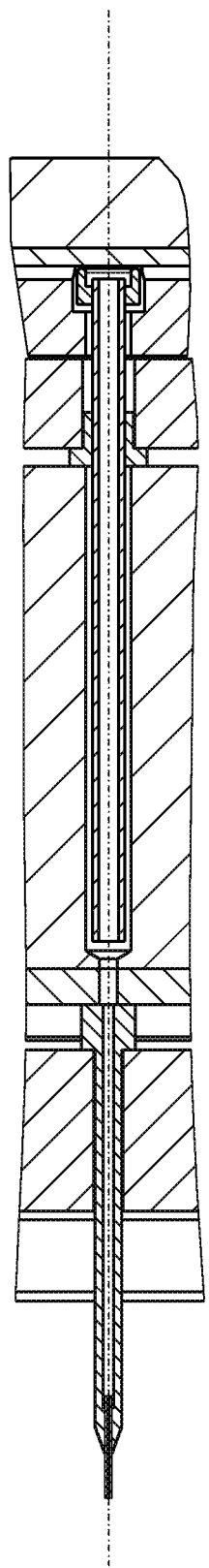
FIG. 3b shows the plunger-cylinder unit according to FIG. 3a in a lower end position of the plunger module.

An embodiment of a plunger-cylinder unit 17 is shown in FIGS. 3a and 3b, and the plunger module 15 is depicted in an upper end position in FIG. 3a, whereas it is depicted in a lower end position in FIG. 3b.

The plunger-cylinder unit 17 comprises an inner cylinder 1.1 and a plunger 5 that is arranged concentrically on a shared axis A with the inner cylinder 1.1. Likewise arranged on the axis A is a capillary 8 that is pneumatically in communication with the inner cylinder 1.1. The plunger 5 is a hollow plunger that is open on both sides and that can be closed on one side.

The inner cylinder 1.1 of a plunger-cylinder unit 17 is formed by a through opening in the carrier plate 1. As shown, this can be a stepped hole comprising a section with a larger inner diameter in which the plunger 5 runs, and a section with a smaller diameter that forms a channel whose diameter is larger than the diameter of the capillaries 8, but smaller than the diameter of a tip collar 7.2 formed on the capillary holder 7. The length of the section in which the plunger 5 runs is selected as a function of the path of travel and of the axial play that the plunger head 5.1 has in a recess 3.1 of the plunger plate 3, which, together with the diameter of the plunger 5, determines the maximum dispensing volume. The smaller the grid in which the capillaries 8 are arranged, the smaller the diameter of the inner cylinder 1.1 necessarily has to be dimensioned, and consequently the greater the length of the section in which the plunger 5 runs has to be.

In order to seal off the plunger 5 with respect to the inner cylinder 1.1, a sealing sleeve 11 that tightly surrounds the plunger 5 is provided between the pressure plate 2 and the carrier plate 1.

The carrier plate 1 with the inner cylinders 1.1 configured in a matrix-shaped arrangement, the pressure plate 2 with through openings in the same arrangement as the inner cylinder 1.1, and a corresponding number of sealing sleeves 11 together form the same number of cylinder modules 16 as there are capillaries 8.

The plunger 5 of a plunger-cylinder unit 17 is a hollow plunger at whose upper end a plunger 5.1 is installed or formed. The plunger head 5.1 surrounds the upper end of the plunger 5 like a cuff, and it has two faces 5.1.1 and 5.1.2 running perpendicular to the axis A. Via the bottom face 5.1.1, the plunger head 5.1 can rest in a recess 3.1 of the plunger holding plate 3 that is deeper than the height of the plunger head 5.1. In this manner, in the direction of the axis A, the plunger head 5.1 has axial play that is equal to the difference between the height of the plunger head 5.1 and the depth of the recess 3.1. The upper face 5.1.2 protrudes beyond the upper end of the plunger 5, as a result of which it can be placed against the plunger seal, which is configured as a plunger sealing plate 6.

Fundamentally, the upper end of the plunger 5 can also protrude beyond the upper face 5.1.2, as a result of which the upper end of the plunger 5 can be placed against the plunger sealing plate 6.

As can be seen in FIG. 1a, the top of the plunger holding plate 3 has a plurality of recesses 3.1 in a matrix-shaped grid like that of the capillaries 8. The recesses 3.1, which are arranged in a row, are connected to each other via grooves 3.2 that together with the plunger seal that is resting on the recesses 3.1 and that is configured as a plunger sealing plate 6, form the air channels. Above the plunger sealing plate 6, there is a stop plate 4 that is affixed by detachable connections indirectly to the plunger holding plate 3 via the plunger sealing plate 6.

The plunger holding plate 3 and the stop plate 4 can be moved together along the axis A relative to the stationary carrier plate 1, as a result of which the plunger 5 can be raised and lowered in the inner cylinder 1.1 along the length of the path of travel.

The plunger holding plate 3, the plunger sealing plate 6, the stop plate 4 as well as the plungers 5 with their associated plunger head 5.1 together form the same number of plunger modules 15 as there are capillaries 8.

The capillary 8 associated with a plunger-cylinder unit 17 is pneumatically connected to the inner cylinder 1.1. Fundamentally, any type of connection can be used here that constitutes a connection that creates a seal with respect to the surroundings.

In order to connect a matrix-shaped arrangement of capillaries 8 to a capillary dispenser, the capillaries 8 are inserted into a cartridge 9 at the appropriate grid distances from each other, and the cartridge 9 is then placed with a positive fit onto the carrier plate 1 indirectly via the sealing mat 10. Below, the term cartridge 9 will refer to a flat plate in which the capillaries 8 are arranged, irrespective of how they are held in the plate and whether they are fastened detachably or undetectably to the plate, or whether they are held without being attached.

In another advantageous embodiment, the capillaries 8 can be, for example, permanently sunk into a cartridge 9. A drawback here is that damaged, broken or clogged capillaries 8 cannot be replaced, which might make it necessary to replace the entire cartridge 9.

Instead, the capillaries 8 can also be secured individually in shafts made, for instance, of plastic, and they can be detachably affixed to a cartridge 9 by means of a screwed, clamped or plug-in connection that is detachably provided on the shaft. The obvious advantage in comparison to the above-mentioned approach is that the capillaries 8 having shafts that are connected to the cartridge 9 with a positive or non-positive fit can be easily replaced individually. The disadvantage is that such connections cannot be opened up repeatedly without sustaining wear, and the tightening force needed to secure the connection must be neither too great nor too small so as not to damage the shaft, while nevertheless ensuring a tight fit.

As an advantageous approach for securing the capillaries 8, the proposal is made to insert each of them into a capillary holder 7 that is configured like a pipette tip as shown in FIGS. 3a and 3b. It consists of a tubular tip part 7.1 and a tip collar 7.2 that is configured on the rear end as seen in the dispensing direction, and that has a front and a rear face facing the tip part 7.1.

The capillary holders 7 can be inserted with their tip part 7.1 into holes provided for this purpose in a cartridge 9 until the rear face of the tip collar 7.2 comes to rest against the cartridge 9, and the capillary holder 7 is suspended in the cartridge 9 with a minimum amount of radial play. In order to replace the capillary holders 7 and thus the capillaries 8, there is no need to release any connections, but rather, the capillary holder 7 is merely pulled out of the cartridge 9 by being lifted without encountering any resistance, which is why the replacement does not exert a mechanical load on the capillary holder 7, meaning that it does not cause any wear and tear.

The capillary 8 is fastened to the front end of the capillary holder 7 in a way that it protrudes from it at least slightly. The capillary 8 can be, for example, glued in or pressed in. The capillary holder 7 advantageously can also be made as a monolithic injection-molded part with the capillary 8 as an insertable part.

The cartridge 9 can be positioned on or fastened to the carrier plate 1, namely, in such a manner that the front faces of the tip collar 7.2 make contact with the sealing mat 10 with a positive fit.

The capillaries 8 are preferably made of glass but they can also be made of other materials such as, for instance, plastic or ceramic, whereby it must be ensured that the capillary rise of the liquid to be dispensed is sufficient to completely fill the capillary 8. The capillary rise h can be calculated according to the following formula:

$$h = \frac{2\gamma\cos\Theta}{\rho g R}$$

wherein $\gamma$ stands for the surface tension of the liquid, $\Theta$ for the wetting angle, $\rho$ for the density of the liquid, g for the gravitational acceleration and R for the inner radius of the capillary 8.

The capillaries 8 preferably have a hydrophobic outer coating so that, to the greatest extent possible, the liquid can be prevented from adhering to the capillary when it is lifted out of the liquid as well as to suppress the tendency of the liquid to creep up on the outside of the capillary 8 when a drop has formed at the end of the capillary. A coating made of fluoropolymer is particularly advantageous.

Advantageously, the capillaries 8 or their free ends are configured with walls that are as thin as possible in order to minimize the size of the face at the end of the capillary, thus minimizing the capacity of the liquid to adhere to the face.

The mode of operation of a capillary dispenser according to an embodiment of the invention will be elaborated upon on the basis of the function of the plunger-cylinder unit 17 as is shown in FIGS. 3a and 3b, in conjunction with the capillary 8 shown.

At the beginning of the dispensing procedure, the plunger module 15 is in an upper end position as depicted in FIG. 3a. The plunger head 5.1 is in contact with the bottom of the recess 3.1 in the plunger holding plate 3. Consequently, ambient pressure is present in the plunger 5, whose lower end is located in the inner cylinder 1.1, while its upper end is in communication with the atmosphere via the air channels.

Since the capillary 8 fills automatically due to the capillary effect when its free end is dipped into the liquid, as long as the other end is open and the ambient pressure at the free end is essentially identical, the capillary 8 can already have been filled or else be filled when it is dipped into a liquid. For this purpose, a vessel filled with the liquid is raised towards the capillaries 8.

For the dispensing procedure, pressure has to be built up in the inner cylinder 1.1, which presupposes that the inner cylinder 1.1 is closed and that the free volume in it is subsequently reduced in order to expel the liquid from the capillary 8. The inner cylinder 1.1 is closed indirectly by closing the plunger 5 on one side by lowering the plunger module 15. After a path that is equal to the axial play of the plunger head 5.1 has been traversed, the plunger head 5.1 is pressed indirectly via the plunger sealing plate 6 onto the stop plate 4, and then closed. As a result, the plunger-cylinder unit 17 is sealed off with respect to the surroundings and, when the plunger module 15 and thus the plunger 5 is lowered further, pressure for dispensing the liquid from the capillaries 8 builds up until it is sufficient to expel the liquid. In this context, see FIG. 3b. A lower end position of the plunger module 15 is reached when the plunger holding plate 3 makes contact with the pressure place 2, but it can also be defined by additional stops that may be present.

After all of the liquid has been dispensed, the plunger 5 is returned to its upper end position in that the plunger module 15 is raised, a process in which the plunger 5 opens up once again, so that ambient pressure is once again established in the inner cylinder 1.1. During or subsequent to this process, liquid can once again be picked up via the capillary 8, whereby this is not done by suction but rather exclusively due to the capillary effect. The described mode of operation takes place synchronously for all of the plunger-cylinder units 17 of the capillary dispenser.

In another embodiment, the number of capillaries 8 in the capillary dispenser is a whole-number multiple of the number of plunger-cylinder units 17 of the type described in the previously described embodiment.

Here, a number of capillaries 8 are connected to each inner cylinder 1.1, corresponding to the multiple of the plunger-cylinder units 17. As the number of capillaries 8 that are to be emptied by the plunger-cylinder unit 17 increases, there is a need to build up a higher pressure in the inner cylinder 1.1.

Instead of a plunger sealing plate 6 as the plunger seal for all of the plunger-cylinder units 17, it is also possible to employ, for example, one ball 12 per plunger-cylinder unit 17 in order to seal off the plunger 5, said ball being inserted into a depression 13.1 located in an additional auxiliary plate 13.

Figure 4B:
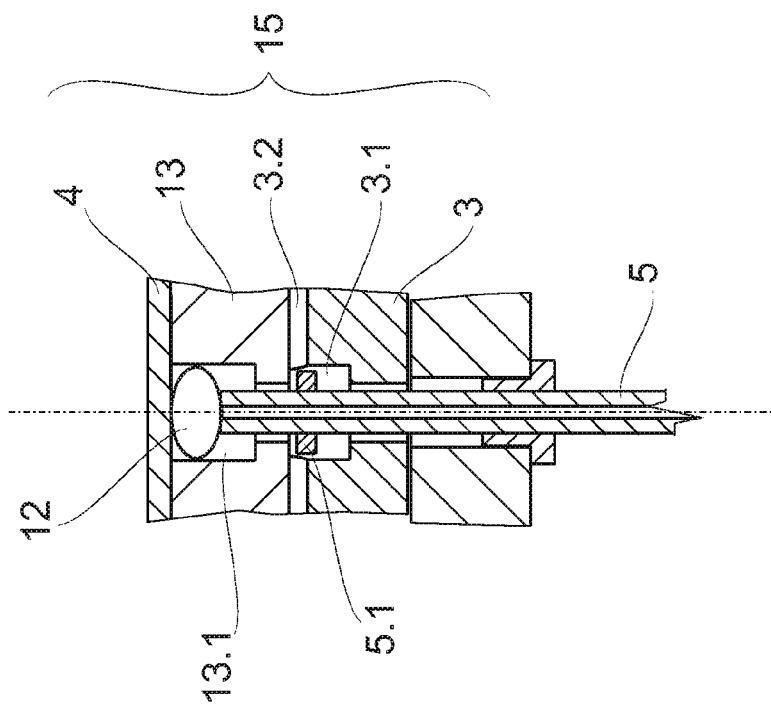
FIG. 4b shows part of a plunger-cylinder unit with the plunger sealed by a ball with the plunger module in a lower end position.
Figure 4A:
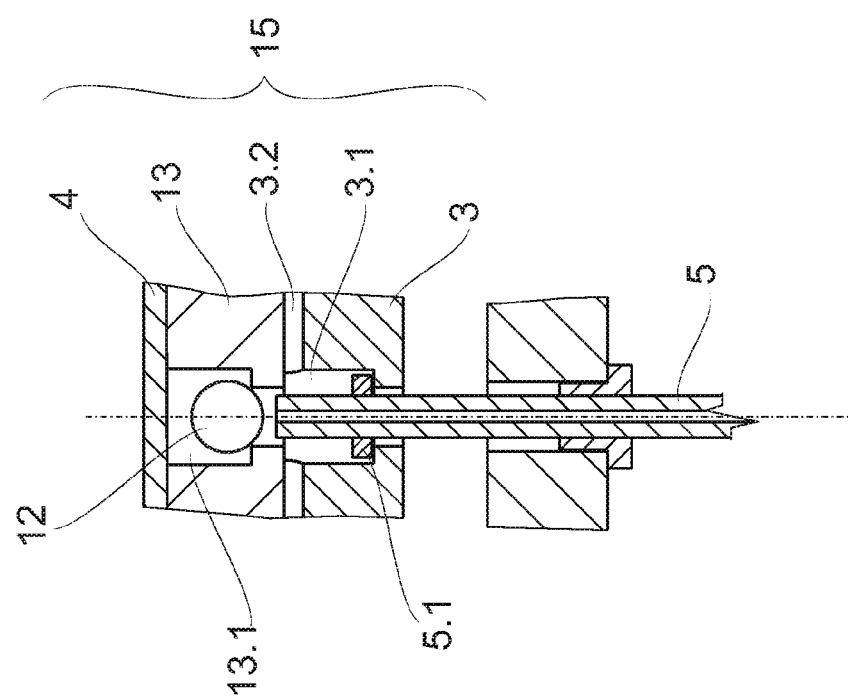
FIG. 4a shows part of a plunger-cylinder unit with another embodiment of a plunger sealed by means of a ball with the plunger module in an upper end position.

FIGS. 4a and 4b show a section of a plunger module 12 with a ball 15 as the plunger seal, in an upper end position and in a lower end position of the plunger module 15.

Like in the previously described embodiment, when the plunger module 15 is in the lower end position, the plunger head 5.1 is in contact with the bottom of the recess 3.1 and the plunger 5 is open.

When the plunger module 15 is in the upper end position, the upper end of the plunger 5 is in direct contact with the ball 12 and the plunger 5 is closed. The ball 12 can be made of an elastomer or of glass, metal or ceramic, with a high-precision surface. In the case of a non-elastic ball 12, the upper end of the plunger 5 is configured with a face with a curvature radius that is equal to the radius of the ball. The balls 12 are each placed above the individual plungers 5 in an auxiliary plate 13 into depressions 13.1 provided for this purpose. In this embodiment as well, grooves 3.2 are provided in the plunger holding plate 3. They can also be created correspondingly in the adjacent side of the auxiliary plate 13.

Figure 5:
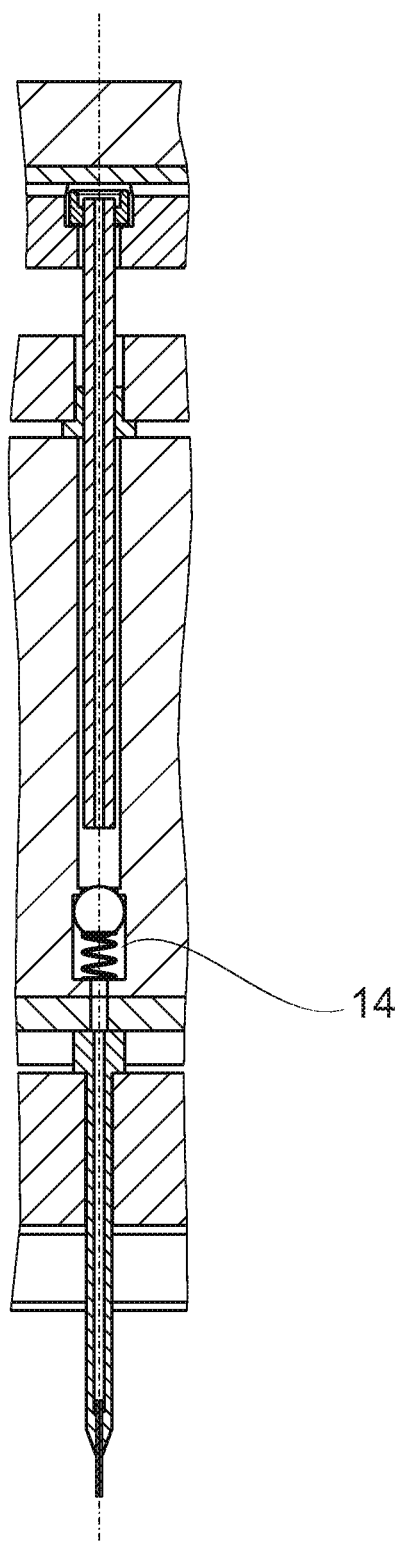
FIG. 5 shows a plunger-cylinder unit with a valve.

Another embodiment will be explained on the basis of FIG. 5.

For a contactless dispensing procedure, as already described in the state of the art, a high plunger acceleration or plunger speed is needed in order to quickly build up the pressure needed for the dispensing procedure. This could be achieved by means of a large plunger diameter. However, if only one capillary 8 is associated with each inner cylinder 1.1, the installation space for this is limited by the grid of capillaries 8 that matches the grid of the wells of the target plates (plate with 96 wells=9 mm; plate with 384 wells=4.5 mm; plate with 1536 wells=2.25 mm).

In order to make do without high accelerations or speeds, it is also possible to install a valve 14 at the lower end of the inner cylinder 1.1. Using the valve 14, the pressure needed in the inner cylinder 1.1 for the dispensing procedure can be built up by means of the plunger 5, after which it is released as a pressure pulse. Not only electromagnetic miniature valves but also passive non-return ball valves as well as so-called duckbill valves or cross-slit valves made of an elastomer are all options in this context. The problem with passive valves is that they typically do not release the pressure as a pulse, but rather, they open slowly when a given threshold has been reached. In order to nevertheless generate a pressure pulse with passive valves, the proposal is made to dimension the valve 14 in such a way that it is always still closed at a maximum possible pressure in the inner cylinder 1.1 and is only mechanically opened when the plunger 5 makes contact, so that the pressure can escape abruptly.

While the invention has been particularly shown and described with reference to preferred embodiments thereof, it will be understood by those skilled in the art that various changes in form and details may be made therein without departing from the spirit and scope of the invention.

LIST OF REFERENCE NUMERALS 1 carrier plate
1.1 inner cylinder
2 pressure plate
3 plunger holding plate
3.1 recess
3.2 groove
4 stop plate
5 plunger
5.1 plunger head
5.1.1 lower face of the plunger head
5.1.2 upper face of the plunger head
6 plunger sealing plate
7 capillary holder
7.1 tip part
7.2 tip collar
8 capillary
9 cartridge
10 sealing mat
11 sealing sleeve
12 ball
13 auxiliary plate
13.1 depression
14 valve
15 plunger module
16 cylinder module
17 plunger-cylinder unit
A axis

The invention claimed is:

1. A capillary dispenser for dispensing a liquid out of at least one capillary comprising:
at least one plunger-cylinder unit including
a cylinder module defining an axis and having an inner cylinder that is pneumatically connected to at least one capillary, and
a plunger module disposed on the axis and including a hollow plunger having open ends at both sides, the plunger being movable in the inner cylinder along the axis between an upper end position and a lower end position of the plunger module, the plunger being closable at one end so as to remain closed over an entire length of a path of travel of the plunger when being moved towards a lower end position so as to compress air present in the plunger-cylinder unit and dispense the liquid by the compressed air, and
wherein the plunger module is associated with a plunger seal configured to receive an upper face of the plunger with a positive fit when the plunger module is in the upper end position so as to close the plunger, the plunger having axial play in a direction of the axis inside the plunger module.

2. The capillary dispenser recited in claim 1, wherein the plunger has a plunger head protruding beyond an upper face of the plunger that is configured to provide the positive fit against the plunger seal when the plunger module is in the upper end position so as to close the plunger.

3. The capillary dispenser recited in claim 2, wherein the plunger seal is a ball and the upper face of the plunger includes a curvature radius that is equal to a radius of the ball.

4. The capillary dispenser recited in claim 2, wherein the plunger seal is a plunger sealing plate.

5. The capillary dispenser recited in claim 1, wherein the plunger seal is a ball and the upper face of the plunger includes a curvature radius that is equal to a radius of the ball.

6. The capillary dispenser recited in claim 1, wherein the plunger seal is a plunger sealing plate.

7. The capillary dispenser recited in claim 1, wherein the inner cylinder is in communication with the capillary via a valve.

8. The capillary dispenser recited in claim 1, wherein the at least one capillary is disposed in a capillary holder, the capillary holder having a shape of a pipette tip.

9. The capillary dispenser recited in claim 1, wherein the capillary dispenser includes a plurality of capillaries, each capillary being firmly received in a capillary holder in the form of a pipette tip with a free end of the capillary protruding, the capillary holders being suspended in a cartridge.

10. The capillary dispenser recited in claim 1, wherein the inner cylinder is in communication with several capillaries.

* * * * *